United States Patent
Kim et al.

(10) Patent No.: US 9,657,174 B2
(45) Date of Patent: May 23, 2017

(54) SILOXANE MONOMER, ENCAPSULANT COMPOSITION, ENCAPSULANT AND ELECTRONIC DEVICE

(71) Applicant: CHEIL INDUSTRIES INC., Gumi-si, Gyeongsangbuk-do (KR)

(72) Inventors: Ha-Neul Kim, Suwon-si (KR); Woo-Han Kim, Suwon-si (KR); Yong-Kook Kim, Suwon-si (KR); Chi-Won An, Suwon-si (KR); Eun-Seon Lee, Suwon-si (KR)

(73) Assignee: CHEIL INDUSTRIES, INC., Gumi-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/652,027

(22) PCT Filed: Dec. 6, 2013

(86) PCT No.: PCT/KR2013/011278
§ 371 (c)(1),
(2) Date: Jun. 12, 2015

(87) PCT Pub. No.: WO2014/104609
PCT Pub. Date: Jul. 3, 2014

(65) Prior Publication Data
US 2015/0322096 A1    Nov. 12, 2015

(30) Foreign Application Priority Data

Dec. 26, 2012 (KR) .......................... 10-2012-0153564

(51) Int. Cl.
  C08L 83/04    (2006.01)
  H01L 23/29    (2006.01)
  C07F 7/08     (2006.01)
  C09D 183/04   (2006.01)
  C07F 7/18     (2006.01)
  H01L 33/56    (2010.01)
  C08G 77/48    (2006.01)

(52) U.S. Cl.
  CPC ............ *C08L 83/04* (2013.01); *C07F 7/0867* (2013.01); *C07F 7/0896* (2013.01); *C07F 7/1836* (2013.01); *C08G 77/485* (2013.01); *C09D 183/04* (2013.01); *H01L 33/56* (2013.01); *H01L 23/296* (2013.01); *H01L 2224/48091* (2013.01); *H01L 2224/48247* (2013.01)

(58) Field of Classification Search
  CPC ......... C08G 77/12; C08G 77/50; C08G 77/52
  USPC ....................................... 528/31, 35
  See application file for complete search history.

(56) References Cited

U.S. PATENT DOCUMENTS

| | | | |
|---|---|---|---|
| 4,818,805 A * | 4/1989 | Ikeno .................. | C08L 83/08 525/31 |
| 7,732,553 B2 | 6/2010 | Hawker et al. | |
| 2011/0278640 A1 | 11/2011 | Motallebi et al. | |
| 2012/0046423 A1 | 2/2012 | Koh et al. | |

FOREIGN PATENT DOCUMENTS

| | | |
|---|---|---|
| EP | 1233020 A2 | 8/2002 |
| EP | 1523035 A2 | 4/2005 |
| JP | 2011-184666 A | 9/2011 |
| KR | 10-2004-0047716 A | 6/2004 |
| KR | 10-2006-0084808 A | 7/2006 |
| KR | 10-2010-0103392 A | 9/2010 |
| KR | 10-2011-0085214 A | 7/2011 |
| WO | WO 2011/081325 A2 | 7/2011 |

OTHER PUBLICATIONS

"A New Polycondensation Process for the Preparation of Polysiloxane Copolymers" authored by Rubinsztajn et al. and published in Marcomolecules (2005) 38, 1061-1063.*

* cited by examiner

Primary Examiner — Marc Zimmer
(74) Attorney, Agent, or Firm — Lee & Morse, P.C.

(57) ABSTRACT

A siloxane monomer obtained from a compound represented by Chemical Formula 1 and a compound represented by Chemical Formula 2, an encapsulant composition including the siloxane monomer, an encapsulant obtained by curing the encapsulant composition, and an electronic device including the encapsulant are disclosed.

15 Claims, 4 Drawing Sheets

SILOXANE MONOMER, ENCAPSULANT COMPOSITION, ENCAPSULANT AND ELECTRONIC DEVICE

TECHNICAL FIELD

A siloxane monomer, an encapsulant composition, an encapsulant, and an electronic device including the encapsulant are disclosed.

BACKGROUND ART

A light emitting device such as a light emitting diode (LED), an organic light emitting diode device (OLED), and a photoluminescence (PL) device has been variously applied to a domestic electric device, a lighting device, a display device, various automatic devices, and the like.

The light emitting device may display intrinsic colors of a light emitting material such as blue, red, and green in a light emission part, or white by combining light emitters displaying different colors.

Such a light emitting device may generally include an encapsulant having a packaging or encapsulation structure. Such an encapsulant may be made of a composition for an encapsulant that is a transparent resin being able to externally pass light emitted from a light emission part.

DISCLOSURE

Technical Problem

One embodiment provides a novel siloxane monomer being applicable to an encapsulant composition.

Another embodiment provides an encapsulant composition capable of improving reliability by including the siloxane monomer.

Yet another embodiment provides an encapsulant obtained by curing the encapsulant composition.

Still another embodiment provides an electronic device including the encapsulant.

Technical Solution

According to one embodiment, a siloxane monomer is obtained from a compound represented by Chemical Formula 1 and a compound represented by Chemical Formula 2:

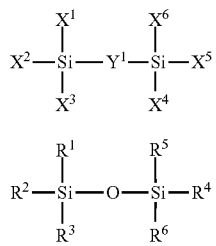

[Chemical Formula 1]

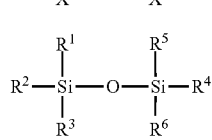

[Chemical Formula 2]

in Chemical Formula 1 or 2, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $X^1$ to $X^6$ are each independently a substituted or unsubstituted C1 to C6 alkoxy group, a hydroxy group, a halogen, a carboxyl group, or a combination thereof, $R^1$ to $R^6$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and at least one of $R^1$ to $R^6$ includes hydrogen.

The compound represented by Chemical Formula 1 may include bis(triethoxysilyl)methane, bis(triethoxysilyl)ethane, bis(triethoxysilyl)vinylene, bis(triethoxysilyl)benzene, bis(triethoxysilyl)biphenyl, bis(trimethoxysilyl)hexane, bis(triethoxysilyl)octane, or a combination thereof.

The siloxane monomer may be represented by Chemical Formula 3.

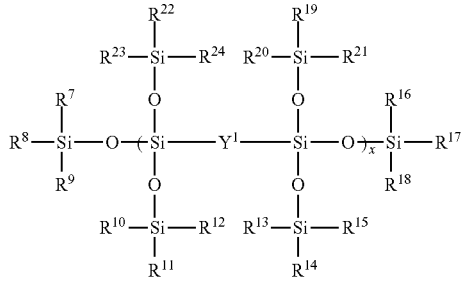

[Chemical Formula 3]

In Chemical Formula 3, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^7$ to $R^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, and x is 1 to 5, $$*\text{-}L^1\text{-}Si\text{---}(OSiR^aR^bR^c)_3 \qquad \text{[Chemical Formula a]}$$

in Chemical Formula a, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^a$, $R^b$ and $R^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and

* indicates a point linked to silicon (Si) of Chemical Formula 3.

At least 30% of terminal end groups of the siloxane monomer may be hydrogen.

According to another embodiment, an encapsulant composition includes a siloxane monomer obtained from a compound represented by Chemical Formula 1 and a compound represented by Chemical Formula 2 and a first polysiloxane having an alkenyl group bound to silicon (Si-Vi) at the terminal end:

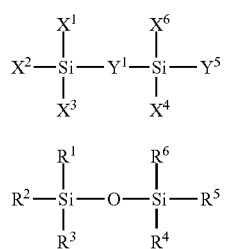

[Chemical Formula 1]

[Chemical Formula 2]

in Chemical Formula 1 or 2, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $X^1$ to $X^6$ are each independently a substituted or unsubstituted C1 to C6 alkoxy group, a hydroxy group, a halogen, a carboxyl group, or a combination thereof, $R^1$ to $R^6$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and at least one of $R^1$ to $R^6$ includes hydrogen.

The compound represented by Chemical Formula 1 may include bis(triethoxysilyl)methane, bis(triethoxysilyl)ethane, bis(triethoxysilyl)vinylene, bis(triethoxysilyl)benzene, bis(triethoxysilyl)biphenyl, bis(trimethoxysilyl)hexane, bis (triethoxysilyl)octane, or a combination thereof.

The siloxane monomer may be represented by Chemical Formula 3.

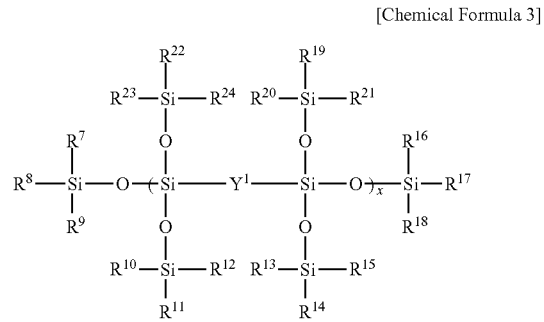

[Chemical Formula 3]

In Chemical Formula 3, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^7$ to $R^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, and x is 1 to 5,

*-L$^1$-Si—(OSiR$^a$R$^b$R$^c$)$_3$ [Chemical Formula a]

in Chemical Formula a, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^a$, $R^b$ and $R^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and

* indicates a point linked to silicon (Si) of Chemical Formula 3.

At least 30% of terminal end groups of the siloxane monomer may be hydrogen.

The siloxane monomer may be included in an amount of about 0.1 to 20 wt % based on the total amount of the encapsulant composition.

The first polysiloxane may be represented by Chemical Formula 4.

$$(R^{25}R^{26}R^{27}SiO_{1/2})_{M1}(R^{28}R^{29}SiO_{2/2})_{D1}(R^{30}SiO_{3/2})_{T1}$$
$$(SiO_{3/2}-Y^2-SiO_{3/2})_{T2}(SiO_{4/2})_{Q1} \quad \text{[Chemical Formula 4]}$$

In Chemical Formula 4,
$R^{25}$ to $R^{30}$ are each independently a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{25}$ to $R^{30}$ includes a substituted or unsubstituted C2 to C30 alkenyl group, $Y^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, 0<M1<1, 0≤D1<1, 0≤T1<1, 0≤T2<1, 0≤Q1<1,
at least one of D1, T1 and T2 is not 0, and
M1+D1+T1+T2+Q1=1.

The first polysiloxane may be included in an amount of about 50 to 99.9 wt % based on the total amount of the encapsulant composition.

The encapsulant composition may further include second a polysiloxane represented by Chemical Formula 5.

$$(R^{31}R^{32}R^{33}SiO_{1/2})_{M2}(R^{34}R^{35}SiO_{2/2})_{D2}(R^{36}SiO_{3/2})_{T3}$$
$$(SiO_{3/2}-Y^3-SiO_{3/2})_{T4}(SiO_{4/2})_{Q2} \quad \text{[Chemical Formula 5]}$$

In Chemical Formula 5,
$R^{31}$ to $R^{36}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{31}$ to $R^{36}$ includes hydrogen, $Y^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, 0M2<1, 0≤D2<1, 0≤T3<1, 0≤T1<1, 0≤Q2<1,
at least one of D2, T3 and T4 is not 0, and
M2+D2+T3+T4+Q2=1.

The second polysiloxane may be included in an amount of about 0.1 to 30 wt % based on the total amount of the encapsulant composition.

Yet according to another embodiment, an encapsulant obtained by curing the encapsulant composition is provided.

The encapsulant may have a transmittance degradation rate of less than or equal to about 10% after heat treatment at about 150° C. after 1000 hours.

Still according to another embodiment, an electronic device including the encapsulant is provided.

Advantageous Effects

Moisture permeability and an oxygen permeability may be lowered and simultaneously heat resistance may be improved by increasing cross-linking density.

BEST MODE

Figure 1:
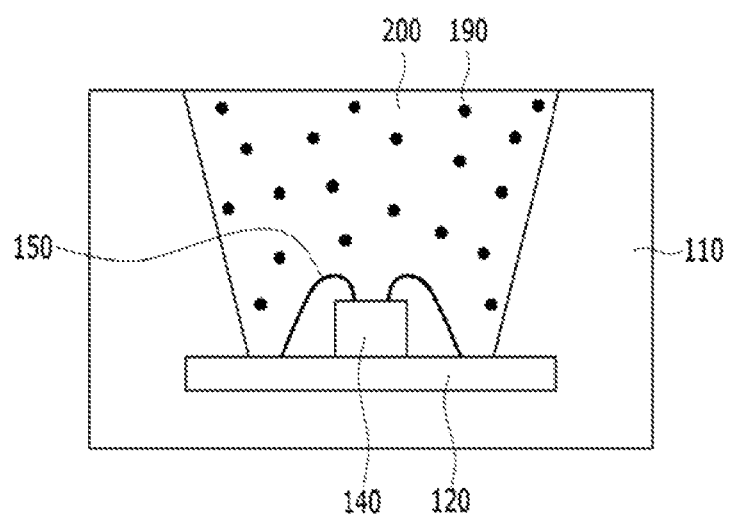
FIG. 1 is a schematic cross-sectional view of a light emitting diode according to one embodiment.

Exemplary embodiments of the present invention will hereinafter be described in detail, and may be easily performed by those who have common knowledge in the related art. However, this disclosure may be embodied in many different forms and is not construed as limited to the exemplary embodiments set forth herein.

In this specification, when a definition is not otherwise provided, 'substituted' refers to one substituted with at least a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, ester group, a carboxyl group or a salt thereof, a sulfonic acid group or a salt thereof, phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof, instead of hydrogen of a compound.

In this specification, when a definition is not otherwise provided, 'hetero' refers to one including 1 to 3 heteroatoms selected from N, O, S, and P.

Hereinafter, a siloxane monomer according to one embodiment is described.

A siloxane monomer according to one embodiment is obtained by a compound represented by Chemical Formula 1 and a compound represented by Chemical Formula 2.

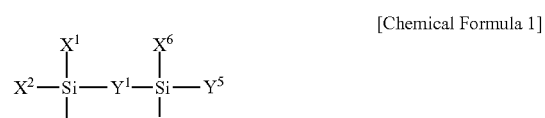

[Chemical Formula 1]

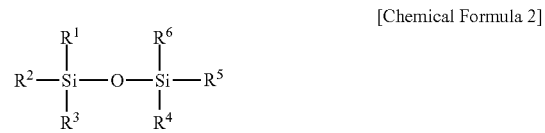

[Chemical Formula 2]

In Chemical Formula 1 or 2, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $X^1$ to $X^6$ are each independently a substituted or unsubstituted C1 to C6 alkoxy group, a hydroxy group, a halogen, a carboxyl group, or a combination thereof, $R^1$ to $R^6$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and at least one of $R^1$ to $R^6$ includes hydrogen.

The compound represented by Chemical Formula 1 is a dipodal compound, for example bis(triethoxysilyl)methane, bis(triethoxysilyl)ethane, bis(triethoxysilyl)vinylene, bis(triethoxysilyl)benzene, bis(triethoxysilyl)biphenyl, bis(trimethoxysilyl)hexane, bis(triethoxysilyl)octane, or a combination thereof.

The compound represented by Chemical Formula 2 is a siloxane compound including at least one hydrogen at the terminal end.

Through a condensation polymerization reaction of the compound represented by Chemical Formula 1 and the compound represented by Chemical Formula 2, a siloxane monomer represented by Chemical Formula 3 may be obtained.

[Chemical Formula 3]

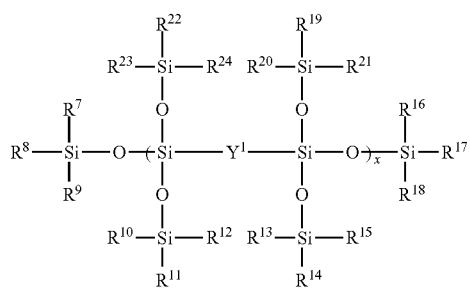

In Chemical Formula 3, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^7$ to $R^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, x is 1 to 5, and $$*\text{-}L^1\text{-}Si\text{---}(OSiR^aR^bR^c)_3 \qquad \text{[Chemical Formula a]}$$

in Chemical Formula a, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^a$, $R^b$ and $R^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and

* indicates a point linked to silicon (Si) of Chemical Formula 3.

At least 30% of terminal end groups of the siloxane monomer may be hydrogen. Preferably, about 50 to 100% of terminal end groups of the siloxane monomer may be hydrogen.

In this way, the compound represented by Chemical Formula 3 includes a large amount of hydrogen bound to silicon (Si—H) moieties at the terminal end and thus reactivity is increased and heat resistance is improved and simultaneously gas permeability and moisture permeability may be improved due to high cross-linking density.

Hereinafter, an encapsulant composition including the siloxane monomer according to one embodiment is described.

An encapsulant composition according to one embodiment includes a siloxane monomer obtained from a compound represented by Chemical Formula 1 and a compound represented by Chemical Formula 2 and a first polysiloxane having an alkenyl group bound to silicon (Si-Vi) at the terminal end.

[Chemical Formula 1]

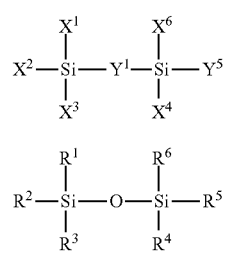

[Chemical Formula 2]

In Chemical Formula 1 or 2, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $X^1$ to $X^6$ are each independently a substituted or unsubstituted C1 to C6 alkoxy group, a hydroxy group, a halogen, a carboxyl group, or a combination thereof, $R^1$ to $R^6$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^1$ to $R^6$ includes hydrogen.

As described above, the siloxane monomer may be represented by Chemical Formula 3.

[Chemical Formula 3]

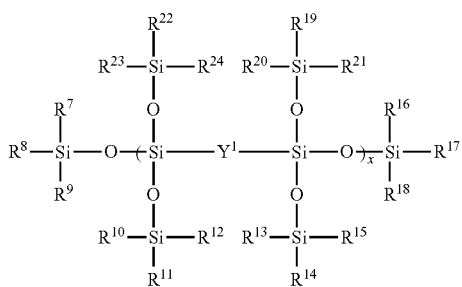

In Chemical Formula 3, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^7$ to $R^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, and x is 1 to 5,

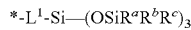 [Chemical Formula a]

In Chemical Formula a, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^a$, $R^b$ and $R^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and

* indicates a point linked to silicon (Si) of Chemical Formula 3.

At least 30%, and preferably about 50 to 100% of terminal end groups of the siloxane monomer may be hydrogen.

One or more kinds of the siloxane monomer may be used.

The siloxane monomer may be included in an amount of about 0.1 to 20 wt % based on the total amount of the encapsulant composition. Within the range, heat resistance, an oxygen permeability, and moisture permeability may be effectively improved. Within the range, it may be included in an amount of about 1 to 15 wt %.

The first polysiloxane may be represented by Chemical Formula 4.

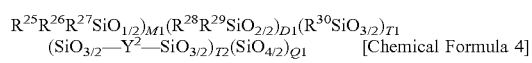 [Chemical Formula 4]

In Chemical Formula 4, $R^{25}$ to $R^{30}$ are each independently a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{25}$ to $R^{30}$ includes a substituted or unsubstituted C2 to C30 alkenyl group, $Y^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $0<M1<1$, $0\le D1<1$, $0\le T1<1$, $0\le T2<1$, $0\le Q1<1$, at least one of D1, T1 and T2 is not 0, and $M1+D1+T1+T2+Q1=1$.

The first polysiloxane is a compound having an alkenyl group bound to silicon (Si-Vi) at the terminal end, and for example may include two or more alkenyl group bound to silicon (Si-Vi) in average. The alkenyl group bound to silicon (Si-Vi) may react with hydrogen positioned at the terminal end of the siloxane monomer.

The first polysiloxane may be, for example obtained by hydrolysis and condensation polymerization of a monomer represented by $R^{25}R^{26}R^{27}SiZ^1$ and at least one selected from a monomer represented by $R^{28}R^{29}SiZ^2Z^3$, a monomer represented by $R^{30}SiZ^4Z^5Z^6$, a monomer represented by $Z^7Z^8Z^9Si-Y^2-SiZ^{10}Z^{11}Z^{12}$, and a monomer represented by $SiZ^{13}Z^{14}Z^{15}Z^{16}$. Herein, $R^{25}$ to $R^{30}$ are the same as defined above, and $Z^1$ to $Z^{12}$ are each independently a C1 to C6 alkoxy group, a hydroxy group, a halogen, a carboxyl group, or a combination thereof.

One or more kinds of the first polysiloxane may be used.

A weight average molecular weight of the first polysiloxane may be about 100 to 30,000 g/mol or about 100 to 10,000 g/mol.

The first polysiloxane may be included in an amount of about 50 to 99.9 wt % based on the total amount of the encapsulant composition. Within the range, the reaction with the first polysiloxane may be effectively performed.

The encapsulant composition may further include a second polysiloxane represented by Chemical Formula 5.

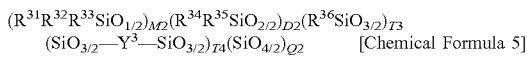

$(R^{31}R^{32}R^{33}SiO_{1/2})_{M2}(R^{34}R^{35}SiO_{2/2})_{D2}(R^{36}SiO_{3/2})_{T3}$
$(SiO_{3/2}-Y^3-SiO_{3/2})_{T4}(SiO_{4/2})_{Q2}$ [Chemical Formula 5]

In Chemical Formula 5, $R^{31}$ to $R^{36}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{31}$ to $R^{36}$ includes hydrogen, $Y^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $0<M2<1$, $0<D2<1$, $0\leq T3<1$, $0\leq T4<1$, $0\leq Q2<1$, at least one of D2, T3 and T4 is not 0, and $M2+D2+T3+T4+Q2=1$.

The second polysiloxane is a compound having hydrogen bound to silicon (Si—H) at the terminal end, and for example may include two or more hydrogen bound to silicon (Si—H) per molecule in average. The hydrogen bound to silicon (Si—H) may react with the alkenyl group positioned at the terminal end of the first polysiloxane.

The second polysiloxane may be, for example obtained by hydrolysis and condensation polymerization of a monomer represented by $R^{31}R^{32}R^{33}SiZ^{14}$, and at least one selected from a monomer represented by $R^{34}R^{35}SiZ^{15}Z^{16}$, a monomer represented by $R^{36}SiZ^{17}Z^{18}Z^{19}$, a monomer represented by $Z^{20}Z^{21}Z^{22}Si-Y^3-SiZ^{23}Z^{24}Z^{25}$, and a monomer represented by $SiZ^{26}Z^{27}Z^{28}Z^{29}$. Herein, $R^{31}$ to $R^{36}$ are the same as defined above, and $Z^{14}$ to $Z^{29}$ are each independently a C1 to C6 alkoxy group, a hydroxy group, a halogen, a carboxyl group, or a combination thereof.

One or more kinds of the second polysiloxane may be used.

A weight average molecular weight of the second polysiloxane may be about 100 to 30,000 g/mol, or about 100 to 10,000 g/mol.

The second polysiloxane may be included in an amount of about 0.1 to 30 wt % based on the total amount of the encapsulant composition.

The encapsulant composition may further include a filler.

The filler may be made of inorganic oxide, for example silica, alumina, titanium oxide, zinc oxide, or a combination thereof.

The encapsulant composition may further include a hydrosilylation catalyst.

The hydrosilation catalyst may accelerate hydroxylation reactions of the first polysiloxane, the second polysiloxane and the third polysiloxane, and it may include, for example platinum, rhodium, palladium, ruthenium, iridium, or a combination thereof.

The hydrosilylation catalyst may be included in an amount of about 0.1 ppm to 1000 ppm based on the total amount of the encapsulant composition.

The encapsulant composition may be cured by be heat-treated at a predetermined temperature and thus may be used as an encapsulant. The encapsulant may be applied to an electronic device for example a light emitting diode and an organic light emitting device.

Hereinafter, as an example of an electronic device to which the encapsulant is applied, a light emitting diode according to one embodiment is described referring to FIG. 1.

FIG. 1 is a schematic cross-sectional view of a light emitting diode according to one embodiment.

Referring to FIG. 1, the light emitting diode includes a mold 110; a lead frame 120 disposed inside the mold 110; a light emitting diode chip 140 mounted on the lead frame 120; a bonding wire 150 connecting the lead frame 120 to the light emitting diode chip 140; and an encapsulant 200 covering the light emitting diode chip 140.

The encapsulant 200 is obtained by curing the encapsulant composition.

A phosphor 190 may be dispersed in the encapsulant 200. The phosphor 190 includes a material stimulated by light and emitting light in an intrinsic wavelength range and largely, a quantum dot such as a semiconductor nanocrystal. The phosphor 190 may include for example a blue phosphor, a green phosphor, a red phosphor, or a mixture of more than two thereof.

The phosphor 190 may display an image in a predetermined wavelength region by light supplied from the light emitting diode chip 140 as a light emission part, and herein, the light emitting diode chip 140 may display a color in a shorter wavelength region than a color displayed in the phosphor 190. For example, when the phosphor 190 displays red, the light emitting diode chip 140 may supply blue or green in a shorter wavelength region than that of the red.

In addition, the color from the light emitting diode chip 140 and the color form the phosphor 190 may be combined and display white. For example, when the light emitting diode chip 140 supplies blue light, and the phosphor 190 includes a red phosphor and a green phosphor, the electronic device may combine blue, red, and green and thus, display white.

The phosphor 190 may be omitted.

MODE FOR INVENTION

Hereinafter, the present disclosure is illustrated in more detail with reference to examples. However, these examples are exemplary, and the present disclosure is not limited thereto.

Synthesis of Siloxane Monomer

Synthesis Example 1

1 kg of a mixed solvent obtained by mixing water and toluene in a weight ratio of 5:5 was put in a 3-necked flask, and 300 g of another mixture obtained by mixing bis (triethoxysilyl)ethane and tetramethyldisiloxane in a molar ratio of 20:80 was added thereto in a dropwise fashion over 2 hours while the mixture was maintained at 65° C. When the addition was complete, the resulting mixture was heated at 70° C. for 5 hours to perform a condensation polymerization reaction. Subsequently, the resultant was cooled down at room temperature, and an aqueous layer was removed therefrom, obtaining a siloxane solution dissolved in toluene. The obtained siloxane solution was rinsed with water to remove a byproduct of organic acid. Subsequently, the neutral siloxane solution was distillated under a reduced pressure to remove the toluene, obtaining a siloxane monomer represented by Chemical Formula 3a.

[Chemical Formula 3a]

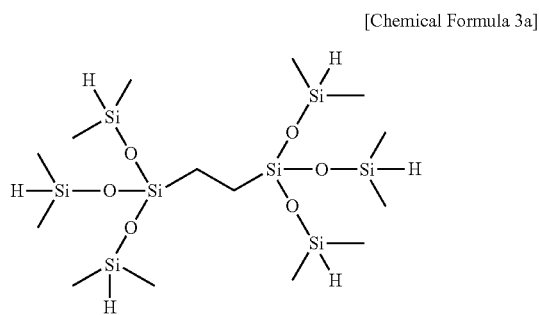 [SMILES: C[SiH](C)O[Si](CC[Si](O[SiH](C)C)(O[SiH](C)C)O[SiH](C)C)(O[SiH](C)C)O[SiH](C)C]

The obtained siloxane monomer had 534 g/mol of a molecular weight reduced to polystyrene when the molecular weight was measured through gel permeation chromatography.

Figure 2:
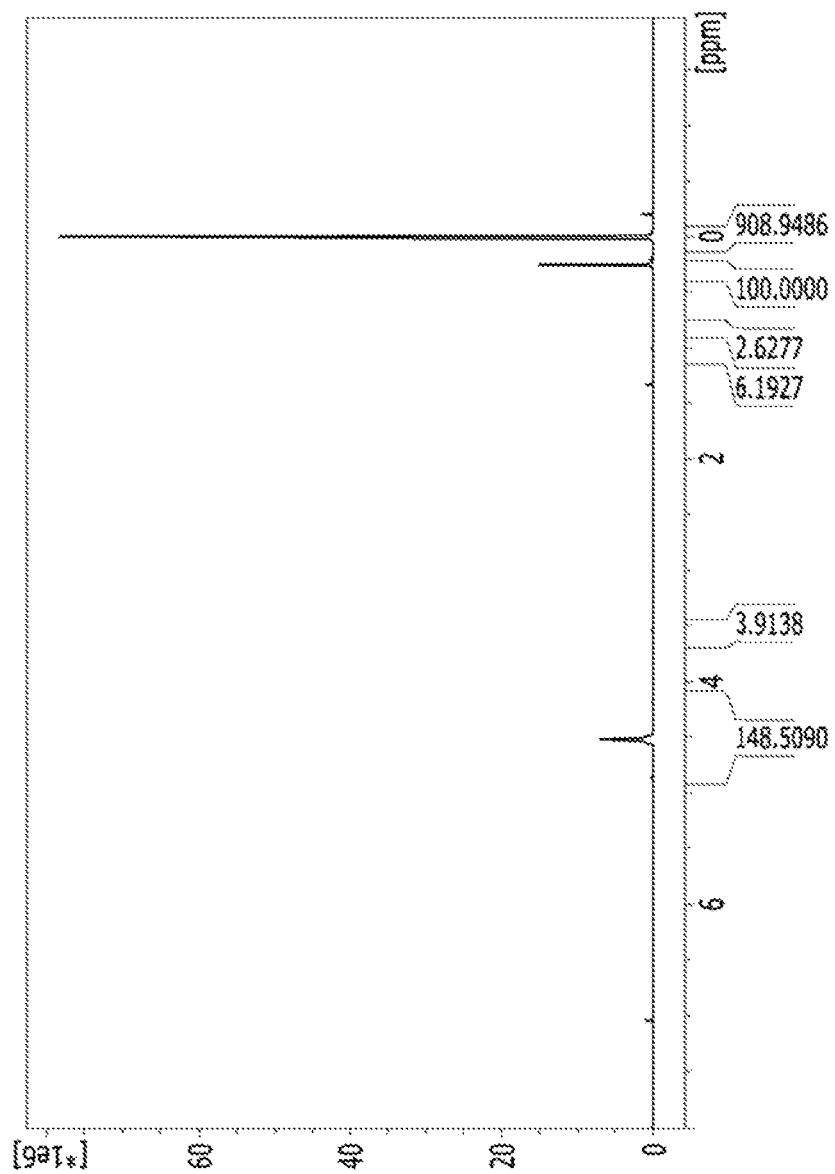
FIG. 2 is a graph showing H-NMR of the siloxane monomer in Synthesis Example 1.

Its H-NMR result is provided in FIG. 2.

FIG. 2 is a graph showing the H-NMR of the siloxane monomer in Synthesis Example 1.

Synthesis Example 2

1 kg of a mixed solvent obtained by mixing water and toluene in a weight ratio of 5:5 was put in a 3-necked flask, and 300 g of a mixture obtained by mixing bis(triethoxysilyl)ethane and tetramethyldisiloxane in a mole ratio of 20:80 was added thereto in a dropwise fashion over one hour while the mixture was maintained at 75° C. When the addition was complete, the resulting mixture was heated at 75° C. for 5 hours to perform a condensation polymerization reaction. Subsequently, the resultant was cooled down to room temperature, and an aqueous layer was removed therefrom, obtaining a siloxane solution dissolved in toluene. The obtained siloxane solution was rinsed with water to remove a byproduct of organic acid. Subsequently, the neutral siloxane solution was distillated under a reduced pressure to remove the toluene, obtaining a siloxane monomer represented by Chemical Formula 3b.

The siloxane monomer had 1602 g/mol of a molecular weight reduced to polystyrene when the molecular weight was measured through gel permeation chromatography.

Figure 3:
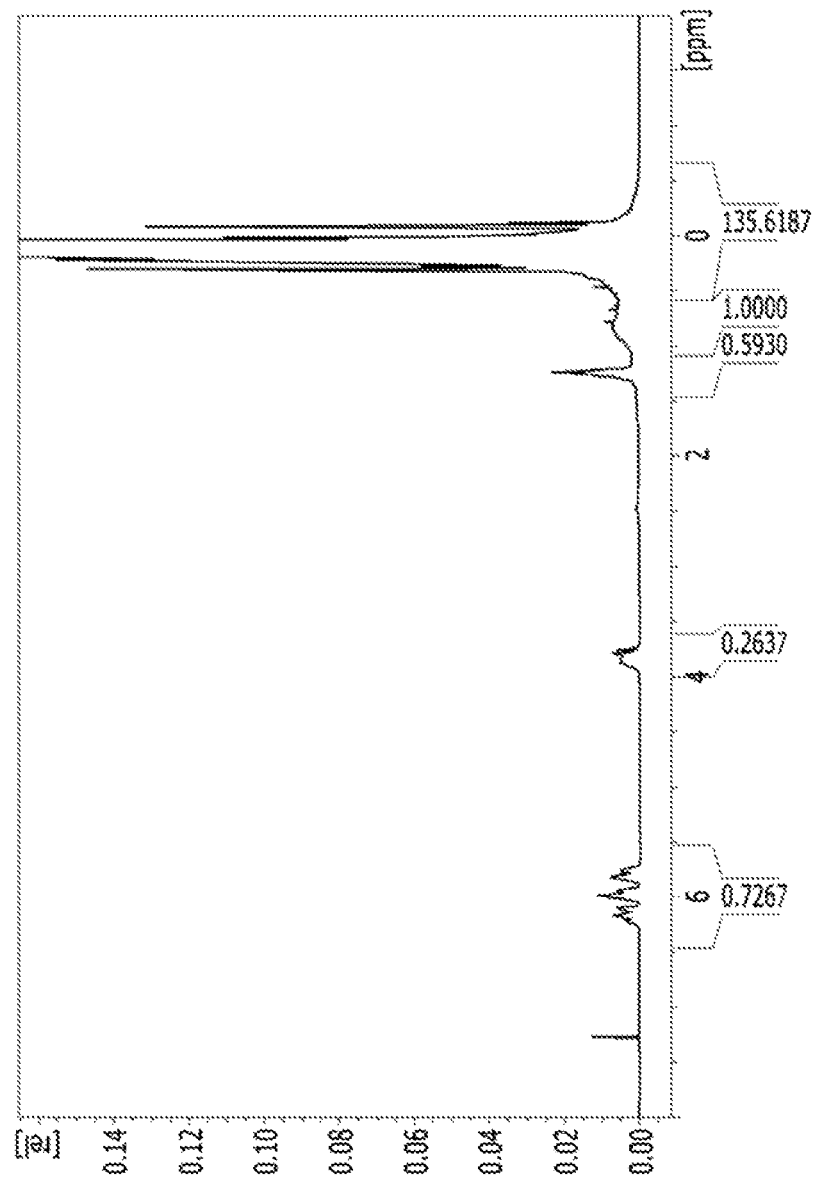
FIG. 3 is a graph showing H-NMR of the siloxane monomer in Synthesis Example 2.

Its H-NMR results are provided in FIG. 3.

FIG. 3 is a graph showing the H-NMR of the siloxane monomer in Synthesis Example 2.

Synthesis Example 3

A siloxane monomer represented by Chemical Formula 3c was prepared according to the same method as Synthesis Example 1 except for using a mixture obtained by mixing bis(triethoxysilyl)benzene and tetramethyldisiloxane in a mole ratio of 40:60 instead of the mixture obtained by mixing bis(triethoxysilyl)ethane and tetramethyldisiloxane in a mole ratio of 20:80.

[Chemical Formula 3c]

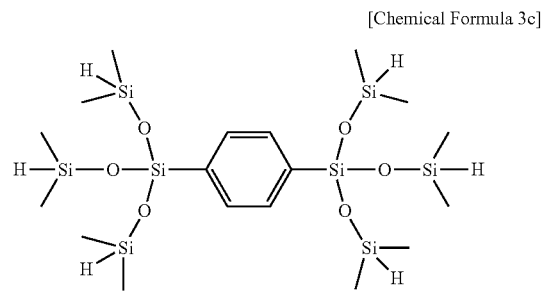 [SMILES: C[SiH](C)O[Si](O[SiH](C)C)(O[SiH](C)C)c1ccc([Si](O[SiH](C)C)(O[SiH](C)C)O[SiH](C)C)cc1]

The siloxane monomer had 583 g/mol of a molecular weight reduced to polystyrene when the molecular weight was measured through gel permeation chromatography.

Synthesis Example 4

A siloxane monomer represented by Chemical Formula 3d was prepared according to the same method as Synthesis Example 2 except for using a mixture of bis(triethoxysilyl)benzene and tetramethyldisiloxane in a mole ratio of 40:60 instead of the mixture obtained by mixing bis(triethoxysilyl)ethane and tetramethyldisiloxane in a mole ratio of 20:80.

[Chemical Formula 3b]

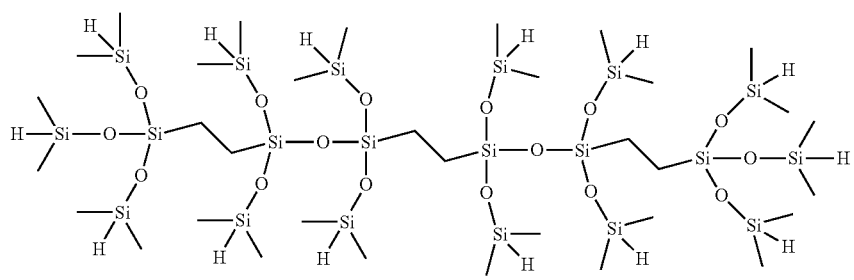

[Chemical Formula 3d]

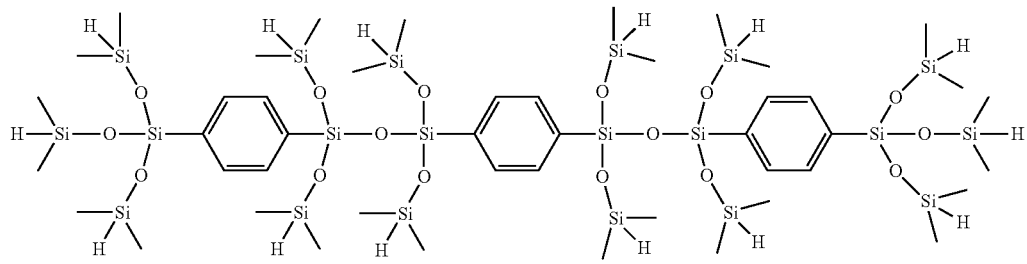

The obtained siloxane monomer had 1749 g/mol of a molecular weight reduced to polystyrene when the molecular weight was measured through gel permeation chromatography.

Comparative Synthesis Example 1

A siloxane monomer represented by Chemical Formula A was prepared according to the same method as Synthesis Example 1 except for using a mixture of diphenyldichlorosilane and tetramethyldisiloxane in a mole ratio of 40:60 instead of the mixture obtained by mixing bis(triethoxysilyl)ethane and tetramethyldisiloxane in a mole ratio of 20:80.

[Chemical Formula A]

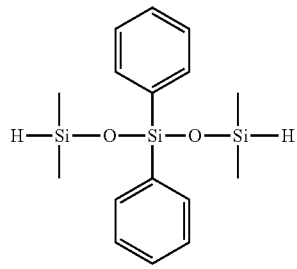

The obtained siloxane monomer had 332 g/mol of a molecular weight reduced to polystyrene when the molecular weight was measured through gel permeation chromatography.

Figure 4:
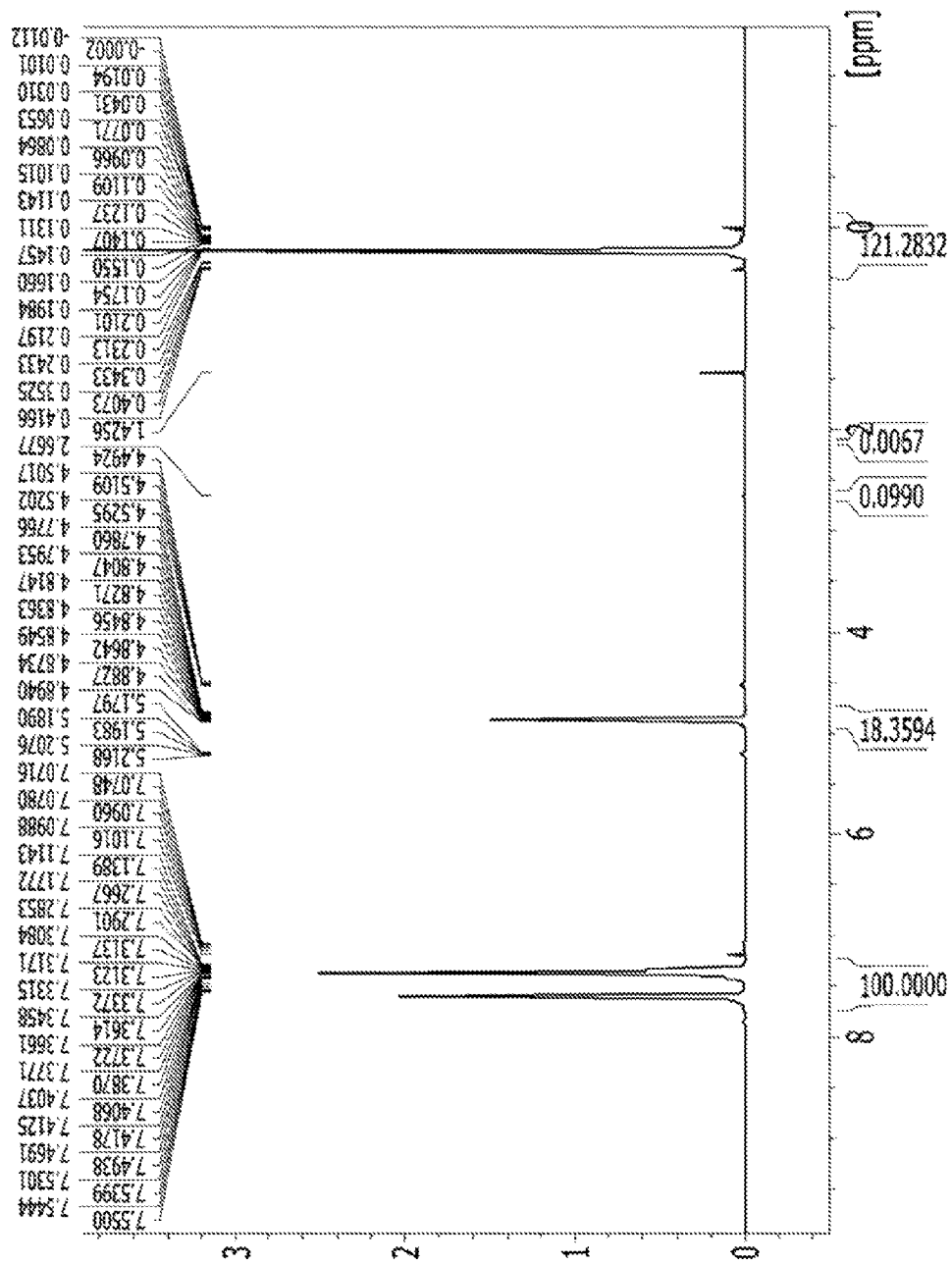
FIG. 4 is a graph showing H-NMR of the siloxane monomer in Comparative Synthesis Example 1.

The H-NMR result is provided in FIG. 4.

FIG. 4 is a graph showing the H-NMR of the siloxane monomer in Comparative Synthesis Example 1.

Evaluation 1

Transmittance and heat resistance of the siloxane monomers according to Synthesis Examples 1 to 4 and Comparative Synthesis Example 1 were evaluated.

The transmittance was measured at a wavelength of 589 nm by using an UV-spectrophotometer (UV-3600, Shimazu Co.) after preparing a 1 mm-thick cured specimen by using each siloxane monomer according to Synthesis Examples 1 to 4 and Comparative Synthesis Example 1.

The heat resistance was measured as a transmittance degradation rate in the same method as above after heat-treating the cured specimen at 150° C. for 1000 hours.

The result is provided in Table 1.

TABLE 1

| | Synthesis Example 1 | Synthesis Example 2 | Synthesis Example 3 | Synthesis Example 4 | Comparative Synthesis Example 1 |
|---|---|---|---|---|---|
| Initial transmittance (%) | 96 | 96 | 96 | 96 | 95 |
| Transmittance after 1000 hours at 150° C. (%) | 92 | 93 | 89 | 90 | 85 |
| Transmittance degradation rate (%) | 4.2 | 3.1 | 7.3 | 6.2 | 10.5 |

Referring to Table 1, the siloxane monomers according to Synthesis Examples 1 to 4 were respectively exposed at a high temperature for a long term but did not become almost yellowish, while the siloxane monomer according to Synthesis Comparative Example 1 was exposed at a high temperature for a long term and became yellowish, showing largely decreased transmittance.

Synthesis of First and Second Polysiloxane

Synthesis Example 5

1 kg of a mixed solvent obtained by mixing water and toluene in a weight ratio of 5:5 was put in a 3-necked flask, and another mixture obtained by mixing 190.40 g of phenyltrichlorosilane and 12.07 g of vinyldimethylchlorosilane was added thereto in a dropwise fashion over 2 hours, while the mixture was maintained at 23° C. When the addition was complete, the resulting mixture was heated at 90° C. for 3 hours to perform a condensation polymerization reaction. Subsequently, the resultant was cooled down to room temperature, and an aqueous layer was removed therefrom, preparing a siloxane solution dissolved in toluene. The obtained siloxane solution was rinsed with water to remove a byproduct of chlorine. The neutral siloxane solution was distilled under a reduced pressure to remove the toluene, obtaining polysiloxane represented by Chemical Formula 4a.

$(Me_2ViSiO_{1/2})_{0.1}(PhSiO_{3/2})_{0.9}$ [Chemical Formula 4a]

(Me: a methyl group, Vi: a vinyl group, Ph: a phenyl group)

The obtained compound had 1450 g/mol of a molecular weight reduced to polystyrene when the molecular weight was measured through gel permeation chromatography.

Synthesis Example 6

1 kg of a mixed solvent obtained by mixing water and toluene in a weight ratio of 5:5 was put in a 3-necked flask, and another mixture obtained by mixing 141.68 g of phenyldichlorosilane, 25.61 g of bis(trichlorosilyl)methane and 6.72 g of tetramethyldisiloxane was added thereto in a dropwise fashion over 2 hours, while the mixture was maintained at 23° C. When the addition was complete, the resulting mixture was heated at 90° C. for 3 hours to perform a condensation polymerization reaction. Subsequently, the resultant was cooled down to room temperature, and an aqueous layer was removed therefrom, preparing a siloxane solution dissolved in toluene. The obtained siloxane solution was rinsed with water to remove a byproduct of chlorine. The neutral siloxane solution was distillated under a reduced pressure to remove the toluene, obtaining polysiloxane represented by Chemical Formula 5a.

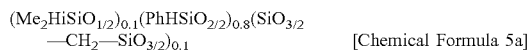

$(Me_2HiSiO_{1/2})_{0.1}(PhHSiO_{2/2})_{0.8}(SiO_{3/2}$—$CH_2$—$SiO_{3/2})_{0.1}$  [Chemical Formula 5a]

(Me: a methyl group, Ph: a phenyl group)

The compound had 5960 g/mol of a molecular weight reduced to polystyrene, when the molecular weight was measured through gel permeation chromatography.

Preparation of Sealant Composition

Example 1

10 wt % of the siloxane monomer obtained in Synthesis Example 1, 70 wt % of the polysiloxane obtained in Synthesis Example 5, 20 wt % of the polysiloxane obtained in Synthesis Example 6, and a hydrosilylation catalyst, Pt—CS 1.8 (Umicore) (added up to a Pt content of 5 ppm) were mixed and foam-removed under vacuum to prepare an encapsulant composition.

Example 2

10 wt % of the siloxane monomer obtained in Synthesis Example 2, 70 wt % of the polysiloxane obtained in Synthesis Example 5, 20 wt % of the polysiloxane obtained in Synthesis Example 6, and a hydrosilylation catalyst, Pt—CS 1.8 (Umicore) (added up to a Pt content of 5 ppm) were mixed and foam-removed under vacuum, to prepare an encapsulant composition.

Example 3

15 wt % of the siloxane monomer obtained in Synthesis Example 3, 65 wt % of the polysiloxane obtained in Synthesis Example 5, 20 wt % of the polysiloxane obtained in Synthesis Example 6, and a hydrosilylation catalyst, Pt—CS 1.8 (Umicore) (added up to a Pt content of 5 ppm) were mixed and foam-removed under vacuum, to prepare an encapsulant composition.

Example 4

15 wt % of the siloxane monomer obtained in Synthesis Example 4, 65 wt % of the polysiloxane obtained in Synthesis Example 5, 20 wt % of the polysiloxane obtained in Synthesis Example 6, and a hydrosilylation catalyst, Pt—CS 1.8 (Umicore) (added up to a Pt content of 5 ppm) were mixed and foam-removed under vacuum, to prepare an encapsulant composition.

Comparative Example 1

20 wt % of the siloxane monomer obtained in Comparative Synthesis Example 1, 60 wt % of the polysiloxane obtained in Synthesis Example 5, 20 wt % of the polysiloxane obtained in Synthesis Example 6, and a hydrosilylation catalyst, Pt—CS 1.8 (Umicore) (added up to a Pt content of 5 ppm) were mixed and foam-removed under vacuum, to prepare an encapsulant composition.

Evaluation 2

Transmittance, heat resistance, refractive index, hardness, moisture permeability and oxygen transmission rates of the encapsulant compositions according to Examples 1 to 4 and Comparative Example 1 were evaluated.

The transmittance was measured by preparing cured specimens having each thickness of 1 mm by using the encapsulant compositions according to Examples 1 to 4 and Comparative Example 1, curing the same, and then using a UV-spectrophotometer (Shimazu Corporation UV-3600) at a wavelength of 589 nm.

The heat resistance was evaluated as a transmittance degradation rate, and then, the transmittance was measured in the same method after heat-treating the cured specimen at 150° C. for 1000 hours.

The refractive index of the encapsulant compositions of Examples 1 to 4 and Comparative Example 1 was measured at a wavelength of D-line 589 nm by using an Abbe refractive index meter.

The hardness was measured by preparing a 5 mm-thick curing specimen with each encapsulant composition according to Examples 1 to 4 and Comparative Example 1 and using a hardness meter of TECLOCK Type A under a pressure of 0.1 MPa.

The moisture permeability and the oxygen permeability were measured by respectively injecting the encapsulant compositions according to Examples 1 to 4 and Comparative Example 1 into a mold with a syringe, curing them at 130° C. for 5 minutes and additionally, at 170° C. for 4 hours, and then, using a moisture permeability equipment (ASTM F-1249, ASTM D-3985) made by MOCON Inc.

The results are provided in Table 2.

TABLE 2

| | Example 1 | Example 2 | Example 3 | Example 4 | Comparative Example 1 |
|---|---|---|---|---|---|
| Transmittance (%) | 98 | 98 | 97 | 97 | 97 |
| Transmittance (%) after heat treatment at 150° C. for 1000 hours | 93 | 94 | 92 | 92 | 86 |
| Transmittance degradation rate (%) | 5.1 | 4.1 | 5.1 | 5.1 | 11.3 |
| Refractive index | 1.52 | 1.52 | 1.53 | 1.53 | 1.54 |
| Hardness (Shore D) | 54 | 53 | 50 | 47 | 45 |
| Moisture permeability (gm/m$^2$day) | 4.0 | 5.4 | 5.7 | 6.1 | 7.1 |
| Oxygen permeability (cc/m$^2$day) | 253 | 333 | 341 | 357 | 382 |

Referring to Table 2, the encapsulant compositions according to Examples 1 to 4 had a similar refractive index to that of the encapsulant composition according to Comparative Example 1 and showed a remarkably deteriorated transmittance degradation rate after allowed to stand at a high temperature for a long term. In addition, the encapsulant compositions according to Examples 1 to 4 showed remarkably improved hardness, moisture permeability and oxygen permeability compared with those of the encapsulant composition according to Comparative Example 1. Accordingly, the encapsulant compositions according to Examples 1 to 4 showed simultaneously improved heat resistance, hardness, moisture permeability and oxygen transmission rate.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. An encapsulant composition, comprising:
a siloxane monomer obtained from a compound represented by Chemical Formula 1 and a compound represented by Chemical Formula 2,
a first polysiloxane represented by Chemical Formula 4, and
a second polysiloxane that is different from the siloxane monomer and is represented by Chemical Formula 5:

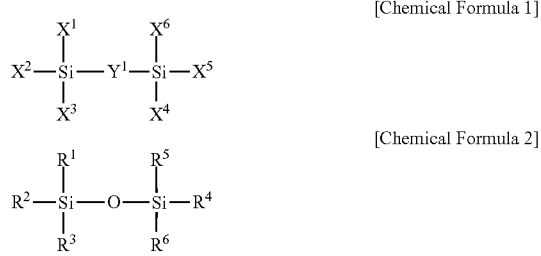

[Chemical Formula 1]

[Chemical Formula 2]

wherein, in Chemical Formulae 1 and 2, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $X^1$ to $X^6$ are each independently a substituted or unsubstituted C1 to C6 alkoxy group, a hydroxy group, a halogen, a carboxyl group, or a combination thereof, $R^1$ to $R^6$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and at least one of $R^1$ to $R^6$ is hydrogen,

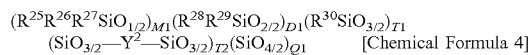

[Chemical Formula 4]

wherein, in Chemical Formula 4, $R^{25}$ to $R^{30}$ are each independently a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{25}$ to $R^{30}$ is a substituted or unsubstituted C2 to C30 alkenyl group, $Y^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $0<M1<1$, $0\le D1<1$, $0\le T1<1$, $0\le T2<1$, $0\le Q1<1$, at least one of D1, T1, and T2 is not 0, and $M1+D1+T1+T2+Q1=1$, and

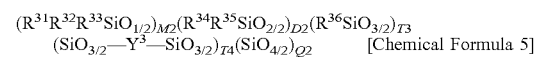

[Chemical Formula 5]

wherein, in Chemical Formula 5, $R^{31}$ to $R^{36}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{31}$ to $R^{36}$ is hydrogen, $Y^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $0<M2<1$, $0\le D2<1$, $0\le T3<1$, $0\le T4<1$, $0\le Q2<1$, at least one of D2, T3, and T4 is not 0, and $M2+D2+T3+T4+Q2=1$.

2. The encapsulant composition of claim 1, wherein the compound represented by Chemical Formula 1 includes bis(triethoxysilyl)methane, bis(triethoxysilyl)ethane, bis(triethoxysilyl)vinylene, bis(triethoxysilyl)benzene, bis(triethoxysilyl)biphenyl, bis(trimethoxysilyl)hexane, bis(triethoxysilyl)octane, or a combination thereof.

3. The encapsulant composition of claim 1, wherein the siloxane monomer is represented by Chemical Formula 3:

[Chemical Formula 3]

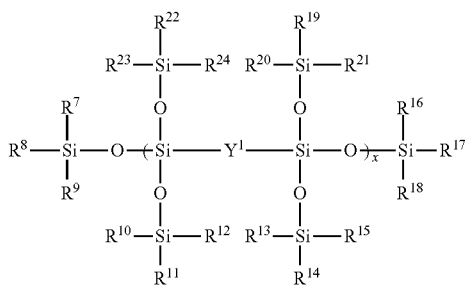

wherein, in Chemical Formula 3, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^7$ to $R^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, and x is 1 to 5, $$\text{*-L}^1\text{-Si}-(\text{OSi}^a R^b R^c)_3 \quad \text{[Chemical Formula a]}$$

wherein, in Chemical Formula a, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^a$, $R^b$, and $R^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and

* indicates a point linked to silicon (Si) of Chemical Formula 3.

4. The encapsulant composition of claim 3, wherein at least 30% of terminal end groups of the siloxane monomer are hydrogen.

5. The encapsulant composition of claim 3, wherein 50 to 100% of terminal end groups of the siloxane monomer are hydrogen.

6. The encapsulant composition of claim 1, wherein the siloxane monomer is included in an amount of 0.1 to 20 wt %, based on a total weight of the encapsulant composition.

7. The encapsulant composition of claim 1, wherein the first polysiloxane is included in an amount of 50 to 99.9 wt %, based on a total weight of the encapsulant composition.

8. The encapsulant composition of claim 1, wherein the second polysiloxane is included in an amount of about 0.1 to 30 wt %, based on a total weight of the encapsulant composition.

9. An encapsulant obtained by curing the encapsulant composition of claim 1.

10. The encapsulant of claim 9, wherein the encapsulant has a transmittance degradation rate of less than or equal to 10% after heat treatment at about 150° C. for 1000 hours.

11. An electronic device comprising the encapsulant of claim 9.

12. The encapsulant composition of claim 1, wherein in Chemical Formula 5, T4 is not 0.

13. The encapsulant composition of claim 3, wherein, in Chemical Formula 3, x is 2 to 5.

14. An electronic device comprising an encapsulant obtained by curing an encapsulant composition, the composition including:
   a siloxane monomer represented by represented by Chemical Formula 3, in which 50 to 100% of terminal end groups of the siloxane monomer are hydrogen,
   a first polysiloxane represented by Chemical Formula 4, and
   a second polysiloxane represented by Chemical Formula 5:

[Chemical Formula 3]

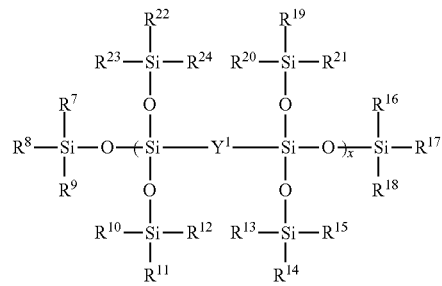

wherein, in Chemical Formula 3, $Y^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^7$ to $R^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, and
x is 1 to 5,

*-L$^1$-Si—(OSiR$^a$R$^b$R$^c$)$_3$  [Chemical Formula a]

wherein, in Chemical Formula a,
L$^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof,
R$^a$, R$^b$, and R$^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and
* indicates a point linked to silicon (Si) of Chemical Formula 3,

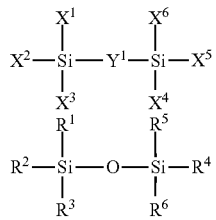

(R$^{25}$R$^{26}$R$^{27}$SiO$_{1/2}$)$_{M1}$(R$^{28}$R$^{29}$SiO$_{2/2}$)$_{D1}$(R$^{30}$SiO$_{3/2}$)$_{T1}$
(SiO$_{3/2}$—Y$^2$—SiO$_{3/2}$)$_{T2}$(SiO$_{4/2}$)$_{Q1}$   [Chemical Formula 4]

wherein, in Chemical Formula 4,
R$^{25}$ to R$^{30}$ are each independently a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof,
at least one of R$^{25}$ to R$^{30}$ is a substituted or unsubstituted C2 to C30 alkenyl group,
Y$^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, 0<M1<1, 0≤D1<1, 0≤T1<1, 0≤T2<1, 0≤Q1<1,
at least one of D1, T1, and T2 is not 0, and
M1+D1+T1+T2+Q1=1, and (R$^{31}$R$^{32}$R$^{33}$SiO$_{1/2}$)$_{M2}$(R$^{34}$R$^{35}$SiO$_{2/2}$)$_{D2}$(R$^{36}$SiO$_{3/2}$)$_{T3}$
(SiO$_{3/2}$—Y$^3$—SiO$_{3/2}$)$_{T4}$(SiO$_{4/2}$)$_{Q2}$   [Chemical Formula 5]

wherein, in Chemical Formula 5,
R$^{31}$ to R$^{36}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof,
at least one of R$^{31}$ to R$^{36}$ is hydrogen,
Y$^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof,
0<M2<1, 0≤D2<1, 0≤T3<1, 0≤T4<1, 0≤Q2<1,
at least one of D2, T3, and T4 is not 0, and
M2+D2+T3+T4+Q2=1.

15. An electronic device comprising an encapsulant obtained by curing an encapsulant composition, the composition including:
a siloxane monomer represented by represented by Chemical Formula 3,
a first polysiloxane represented by Chemical Formula 4, and
a second polysiloxane represented by Chemical Formula 5:

[Chemical Formula 3]

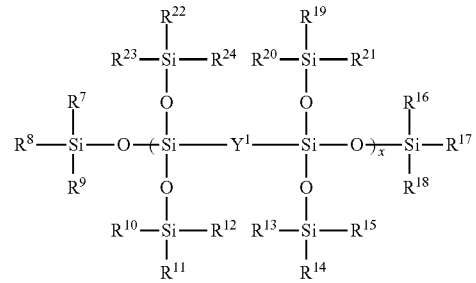

wherein, in Chemical Formula 3,
Y$^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof,
R$^7$ to R$^{24}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, a moiety represented by Chemical Formula a, or a combination thereof, and x is 2 to 5, $$*-L^1-Si-(OSiR^aR^bR^c)_3 \quad \text{[Chemical Formula a]}$$

wherein, in Chemical Formula a, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $R^a$, $R^b$, and $R^c$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, and

* indicates a point linked to silicon (Si) of Chemical Formula 3,

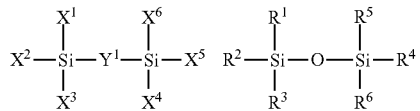

$$(R^{25}R^{26}R^{27}SiO_{1/2})_{M1}(R^{28}R^{29}SiO_{2/2})_{D1}(R^{30}SiO_{3/2})_{T1}\\(SiO_{3/2}-Y^2-SiO_{3/2})_{T2}(SiO_{4/2})_{Q1} \quad \text{[Chemical Formula 4]}$$

wherein, in Chemical Formula 4, $R^{25}$ to $R^{30}$ are each independently a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{25}$ to $R^{30}$ is a substituted or unsubstituted C2 to C30 alkenyl group, $Y^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $0<M1<1$, $0\leq D1<1$, $0\leq T1<1$, $0\leq T2<1$, $0\leq Q1<1$, at least one of D1, T1, and T2 is not 0, and $M1+D1+T1+T2+Q1=1$, and $$(R^{31}R^{32}R^{33}SiO_{1/2})_{M2}(R^{34}R^{35}SiO_{2/2})_{D2}(R^{36}SiO_{3/2})_{T3}\\(SiO_{3/2}-Y^3-SiO_{3/2})_{T4}(SiO_{4/2})_{Q2} \quad \text{[Chemical Formula 5]}$$

wherein, in Chemical Formula 5, $R^{31}$ to $R^{36}$ are each independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 alkynyl group, a substituted or unsubstituted C1 to C30 alkoxy group, a substituted or unsubstituted C1 to C30 carbonyl group, a hydroxy group, or a combination thereof, at least one of $R^{31}$ to $R^{36}$ is hydrogen, $Y^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, or a combination thereof, $0<M2<1$, $0\leq D2<1$, $0\leq T3<1$, $0\leq T4<1$, $0\leq Q2<1$, at least one of D2, T3, and T4 is not 0, and $M2+D2+T3+T4+Q2=1$.

* * * * *